(12) United States Patent
Li et al.

(10) Patent No.: US 12,371,449 B2
(45) Date of Patent: Jul. 29, 2025

(54) METHOD FOR THE PREPARATION OF LYSOPHOSPHATIDYLINOSITOL

(71) Applicant: KEMIN INDUSTRIES, INC., Des Moines, IA (US)

(72) Inventors: Zheng Li, Zhuhai (CN); Songying Li, Zhuhai (CN); Shengshu Huang, Zhuhai (CN)

(73) Assignee: KEMIN INDUSTRIES, INC., Des Moines, IA (US)

( * ) Notice: Subject to any disclaimer, the term of this patent is extended or adjusted under 35 U.S.C. 154(b) by 1136 days.

(21) Appl. No.: 17/235,561

(22) Filed: Apr. 20, 2021

(65) Prior Publication Data
US 2022/0002325 A1 Jan. 6, 2022

Related U.S. Application Data

(60) Provisional application No. 63/051,697, filed on Jul. 14, 2020.

(30) Foreign Application Priority Data

Jul. 6, 2020 (WO) ................ PCT/CN2020/100444

(51) Int. Cl.
*C07F 9/10* (2006.01)
*C12P 7/6436* (2022.01)

(52) U.S. Cl.
CPC ............ *C07F 9/103* (2013.01); *C12P 7/6436* (2013.01)

(58) Field of Classification Search
None
See application file for complete search history.

(56) References Cited

U.S. PATENT DOCUMENTS

| | | | |
|---|---|---|---|
| 4,849,137 A | 7/1989 | Kobayashi | |
| 6,495,532 B1 * | 12/2002 | Bathurst | A61K 31/66 514/18.9 |
| 7,189,544 B2 | 3/2007 | Schmitt et al. | |
| 2010/0260682 A1 | 10/2010 | Ferguson et al. | |
| 2016/0229793 A1 | 8/2016 | Dasari et al. | |
| 2018/0021250 A1 | 1/2018 | Goto et al. | |

FOREIGN PATENT DOCUMENTS

JP 5065370 B2 3/2010

OTHER PUBLICATIONS

International Searching Authority, "Search Report and Written Opinion," issued in connection with International Patent Application No. PCT/US2021/028184, mailed Jul. 16, 2021, 7 pages.
Brautigan et al., "Lysolecithin as feed additive enhances collagen expression and villus length in the jejunum of proiler chickens," Journal of Poultry Science, 2017, available at http://dx.doi.org/10.3382/ps/pex078, 10 pages.
Kim et al., "Production of egg yolk lysolecithin with immobilized phsopholipase A2," Enzyme and Microbial Technology, vol. 29, 2001, pp. 587-592.
Fan et al., "Preparation of soybean lysophospholipids and its biosaftefy analysis," China Oil and Fats, vol. 44, No. 6, 2019, 5 pages.
Hu et al., "Preparation of Lysophospholipids by Phospholipase A1-Catalyzed Hydrolysis of Antarctic Krill Phospholipids in Aqueous Phase," Food Science, vol. 40, No. 12, 2019, 6 pages.
Mnasri et al., "Lipase-catalyzed production of lysophospholipids," Oilseeds & fats Crops and Lipids, vol. 24, No. 4, 2017, 6 pages.

* cited by examiner

*Primary Examiner* — Christian L Fronda
(74) *Attorney, Agent, or Firm* — NYEMASTER GOODE P.C.

(57) ABSTRACT

The present invention relates to a high-LPI lysolecithin and methods related to the same. The high-LPI product is produced through the reaction of lecithin with a unique method using solvent, buffer/water, and phospholipase. Using the current production method, LPI content increased from 1.4% to 3.2-13.1% using regular soy lecithin as the starting material and LPC, LPE and LPA contents also increased from 5.1%, 2.0%, 1.0% to 15.8%, 14.6% and 4.4% respectively.

22 Claims, 6 Drawing Sheets

METHOD FOR THE PREPARATION OF LYSOPHOSPHATIDYLINOSITOL

CROSS-REFERENCE TO RELATED APPLICATIONS

This application claims the benefit of priority to International Patent Application No. PCT/CN2020/100444, filed Jul. 6, 2020, entitled "A METHOD FOR THE PREPARATION OF LYSOPHOSPHATIDYLINOSITOL," and U.S. Provisional Patent Application No. 63/051,697, filed Jul. 14, 2020, entitled "A METHOD FOR THE PREPARATION OF LYSOPHOSPHATIDYLINOSITOL," the entire disclosures of which are hereby incorporated by reference in their entireties.

BACKGROUND OF THE INVENTION

Commercially available lecithin is a family of phospholipids (PL) rich in phosphatidylcholine (PC), phosphatidylinositol (PI), phosphatidylethanolamine (PE) and phosphatidic acid (PA) (FIG. 1). It is well known as a natural surfactant and widely used in food, feed and pharmaceutical industries. Commercial lecithins are usually extracted from soybean, rapeseed, sunflower seed and egg yolk. Lecithins of different resources not only vary in phospholipid type and its content, but also vary in the fatty acid profile at sn-1 and sn-2 position, which makes lecithin a very complex mixture. It is difficult to isolate high-purity phospholipid component, especially LPI from natural lecithin.

Nutrient absorption is highly influenced by the healthy development of intestinal villus. Lysoforte™, a lysolecithin-based product, was confirmed to enhance collagen expression and villus length in the jejunum of broiler chickens[1]. Besides lysophosphatidylcholine (LPC), another primary component in Lysoforte-lysophosphatidylinositol (LPI) was speculated to play a key role. As such, a high purity LPI was needed to confirm such a role. LPI has been reported to be involved in many biological processes, including promotion of protein digestion in animals.

LPI can be synthesized from the partial hydrolysis of PI (Phosphatidylinositol), a major phospholipid component in lecithin, via phospholipase $A_1$ or $A_2$ in an aqueous medium[2,3,4]. Most sources are focused on converting PC (Phosphatidylcholine)/PE (Phosphatidylethanolamine) to LPC/LPE (Lysophosphatidylethanolamine), whereas little information on LPI conversion has been involved (Table 1). It has also been found that LPI content in lysolecithin products is very low—less than 2.5%. Besides an aqueous reaction system, organic solvents are also used for enzymatic modification of lecithin. Kim et al developed a method for producing egg yolk lysolecithin with immobilized phospholipase $A_2$ in an ethanol buffer[5]. Other organic solvents such as hexane, benzene, toluene, cycloalkanes, and petroleum ether were also investigated by researchers[6,7]. However, there are no public reports using ethyl acetate (EtOAc) or isopropyl acetate as the solvent to convert PI to LPI via phospholipase $A_1$(PLA$_1$). Although high pure LPI can be obtained using column chromatography, commercial application, especially in the feed industry, of this method will be limited due to low production.

TABLE 1

Phospholipid profile of soy lecithin (SL) and lysolecithin (LCL) (weight %)

| Lot No. | PC | 1-LPC | 2-LPC | PI | LPI | PE | LPE | PA | LPA | PG |
|---|---|---|---|---|---|---|---|---|---|---|
| SL110824-01 | 14.6 | — | 0.8 | 9.1 | — | 11.7 | 0.4 | 5.2 | 0.2 | 0.6 |
| SL120306-01 | 15.5 | 0.1 | 1.0 | 10.4 | 0.9 | 7.1 | 0.3 | 3.8 | 0.2 | 1.4 |
| SL120413-01 | 15.2 | 0.1 | 0.7 | 11.0 | 0.7 | 8.0 | 0.3 | 4.2 | 0.1 | 0.8 |
| SL120425-01 | 14.6 | 0.1 | 0.9 | 9.5 | — | 8.8 | 0.3 | 3.2 | 0.2 | 0.7 |
| SL120502-01 | 19.2 | 0.1 | 0.9 | 11.1 | — | 9.8 | 0.2 | 1.5 | 0.1 | 0.9 |
| LCL1202100165 | 3.87 | 0.58 | 5.81 | 4.40 | 2.54 | 2.57 | 2.58 | 0.57 | 0.94 | 0.30 |
| LCL1202100166 | 4.86 | 0.58 | 5.92 | 5.51 | 2.24 | 3.00 | 2.70 | 0.67 | 1.01 | 0.34 |
| LCL1202100167 | 5.62 | 0.60 | 5.97 | 5.49 | 2.29 | 2.88 | 2.29 | 0.76 | 1.09 | 0.27 |
| LCL1304100245 | 2.84 | 0.48 | 4.81 | 4.32 | 2.49 | 1.84 | 2.49 | 0.39 | 0.74 | 0.21 |

Kemin has developed different enzymatic hydrolysis methods for the production of lysolecithin. However, the content of LPI in lysolecithin (LCL) is less than 2.5% and the conversion rate of PI to LPI is very low.

There is therefore a need in the industry for an effective means of producing lysolecithin with high LPI content at both lab scale and pilot scales. The ability to produce high-LPI lysolecithin with a low manufacturing cost would provide a great opportunity to use LPI as a nutritional ingredient for animals.

BRIEF SUMMARY OF THE INVENTION

The present invention relates to the preparation of lysolecithin with high LPI content using an acetate or an ether as solvent. A fast and effective work-up procedure was also developed to separate LPI products from the starting material simply by phase separation. The method of the invention surprisingly provides enriched LPC, LPE and LPA content in the high-LPI lysolecithin product of the invention.

The lecithin is combined with an organic solvent, a buffer or water, and a phospholipase to catalyze the hydrolysis of the phospholipids. In one embodiment of the invention, the lecithin is mixed with EtOAc, phosphate buffered solution (PBS) and PLA$_1$ for a period of time sufficient to hydrolyze the phospholipids, after which the resulting lysophospholipids are separated from the mixture then dried. Under optimized conditions, the LPI content achieved higher than 13% while LPC content is likewise increased to greater than 15%. The method of the invention is applicable to synthesis of high-LPI lysolecithin under pilot production conditions.

DETAILED DESCRIPTION OF THE FIGURES

DETAILED DESCRIPTION OF THE INVENTION

Figure 1:
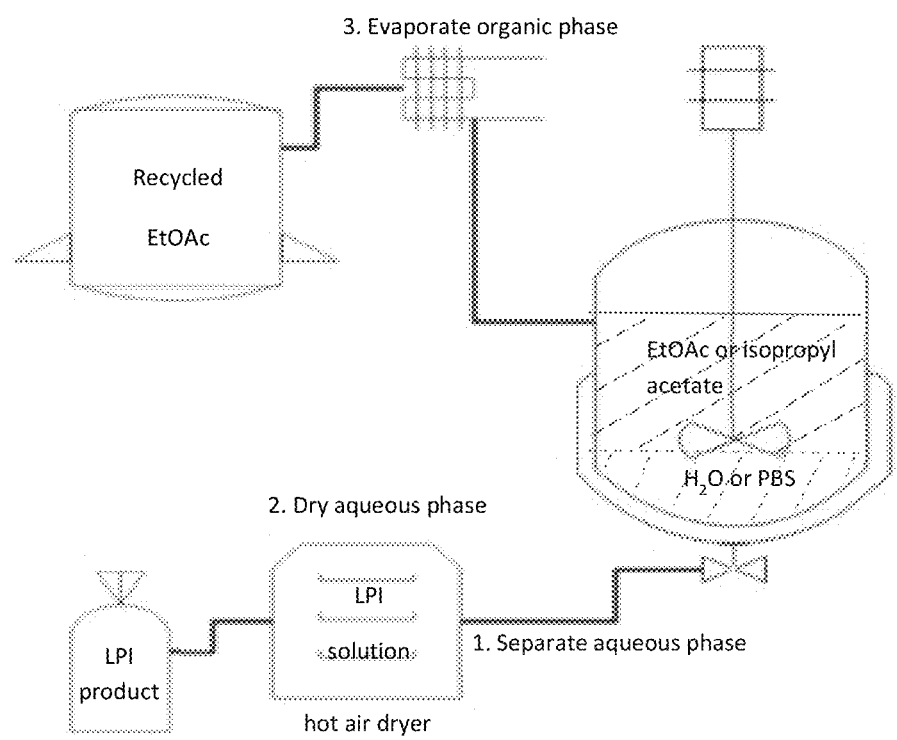
FIG. 1 is s flow chart for pilot production of high-LPI lysolecithin as described in Example 2.

The invention relates to the high-LPI lysolecithin and the processes and methods related to the same. The starting material is lecithin (phosphatidylcholine) and all sources thereof including, but not limited to, soy, sunflower, corn, rapeseed, peanuts, organ meats, red meats, whole eggs, whole milk with cream, spinach, cauliflower, oranges, wheat germ, fish, dairy cream, and liver. The starting material can also be in various forms including, but not limited to liquid, solid, syrup, slurry and paste. In one embodiment of the invention, the sources of lecithin are deoiled lecithin and soy lecithin. The invention is also intended to include other potential natural and synthetic sources of lecithin.

The lecithin is first mixed with a solvent, a buffer, or deionized water, and a phospholipase to catalyze the hydrolysis of the phospholipid. The solvent is one capable of at least partially dissolving the lecithin. Such solvents are well known in the art and include, but are not limited to, methanol, ethanol, acetonitrile, acetone, and ethers and acetates such as diethyl ether, ethyl ether, methyl tert-butyl ether, methyl t-butyl ether (MTBE), isopropyl acetate and ethyl acetate (EtOAc). In one embodiment of the invention, the solvent is EtOAc. The solvent should be included in an amount of at least about 100% volume of solvent to lecithin weight. In one embodiment, the solvent is included in a range of about 300-1200% volume of solvent to lecithin weight, with about 400-600% volume of solvent to lecithin weight being preferred.

Many types of buffers as well as deionized water are appropriate for use in the invention include, but are not limited to, phosphate buffered solution (PBS), modified PBS buffers, borate buffers, Hepes and other Good's buffers, alkaline buffers such as carbonate buffers and Tris-based buffers, and acidic buffers such as citrate buffers. In one embodiment of the invention, the buffer is PBS. In one embodiment, the buffer is included in an amount of at least about 1% by weight buffer to lecithin weight. In one embodiment, the buffer is included in a range of about 20-120% weight of buffer to lecithin weight, with about 30-80% weight of buffer to lecithin weight being preferred.

The phospholipase of the invention may be any phospholipase capable of cleaving the lecithin molecule into fatty acid and other lipophilic substances, which is generally phospholipase $A_1$ or phospholipase $A_2$. In one embodiment of the invention, the phospholipase is phospholipase $A_1$ ($PLA_1$). In one embodiment, the $PLA_1$ is included in an amount of at least about 0.1% by weight $PLA_1$ to lecithin weight. In one embodiment, the $PLA_1$ is included in an amount of 0.2-0.8% by weight $PLA_1$ to lecithin weight, with about 0.3-0.5% by weight $PLA_1$ to lecithin weight being preferred.

The mixture of lecithin, solvent, buffer, and phospholipase is heated to a temperature sufficient to cause hydrolysis of the lecithin. In general, the mixture is heated to a temperature of at least 30° C. for a time period of at least 15 minutes. In one embodiment, the mixture is heated to a temperature ranging from about 40-65° C. for a time period of about 0.5-5 hours, with a temperature less than about 65° C. and a time period of about 3-5 hours being preferred. Following the reaction, the $PLA_1$ is heated to a temperature and for a time period sufficient to deactivate the enzyme, which is generally a temperature of at least 70° C. for at least 30 minutes.

The hydrolyzed mixture is next cooled to a temperature and for a time period sufficient to allow the phase separation to occur, which is generally to a temperature of 40° C. or less and a time period of at least 30 minutes. The lysolecithin component settles into the aqueous phase at the bottom while the oil and free fatty acid remain in the solvent phase on the top. The aqueous phase is collected and dried using procedures known in the art including, but not limited to, spray drying, drum drying, freeze drying, microwave drying, convective drying, conductive drying, air drying, etc. In one embodiment, the solution is dried to 20% by weight or less moisture. In another embodiment, the solution is dried to a moisture content of about 10% by weight or less. The organic phase is either discarded or recycled.

The final composition contains a substantially higher percentage of LPI, with LPI content increased from about 1.4% to 6.5% when using regular soy lecithin as the starting material. Furthermore, average LPC content substantially increased from about 5% to 15% or higher. LPA content was also significantly higher. Overall, the invention provides a cost-effective, environmentally friendly and efficient way to prepare high-LPI, high-LPC, and high-LPA lysolecithin.

The compositions of the present invention may optionally be combined with a pharmaceutically acceptable carrier that may include one or more carriers or excipients, such as fillers, diluents, binders, lubricants, and disintegrants. Such ingredients and their relative amounts to be included are well known to persons skilled in the art.

Obtaining high LPI content lysolecithin is difficult for two reasons—the difficulty to control hydrolysis extent of PI to LPI and the lack of purification method to enrich LPI from the hydrolysis mixture. In order to improve the hydrolysis of PI, either large quantity of water or excess amount of enzymes like phospholipase A1 and A2 is needed. Hydrolysis under such intense conditions usually cleaves one fatty acid chain to afford LPI, or possibly cleaves two fatty acid chains to afford glycosylphosphatidylinositol (GPI). It's important to have PI hydrolyzed to LPI at high ratio but not over hydrolyzed to GPI if we want the product to contain high level of LPI. D. M. Cabezas et al[1] reported a method of using phospholipase A2 to hydrolyze sunflower lecithin in a lecithin-water emulsion system. The hydrolysis ratio of PI to LPI that could be reached is as high as 75.7%, but it could only give product with LPI up to 7.0% by weight after drying of reaction mixture due to lack of purification method. Prior art (Japanese Patent JP2010063470A)[2] also reported an enzyme reaction carried out in an aqueous medium to push lecithin to a high hydrolysis extent, followed by a work-up procedure using acetone precipitation and hexane-ethanol-water extraction system to enrich LPI. LPI could be enriched to as high as 71% but the yield was very low (<10%). Heidi Schmitt et al[3] reported enzymatic hydrolysis of soy lecithin by using phospholipase A1/A2 in combination with lipase. The method hydrolyzed lecithin to lysolecithin but no LPI content was tested for the process. Toshihiko Aiba et al[4] and Marco Falasca[5] et al reported chemical synthesis to obtain LPI at high purity. They were both multi-step organic synthesis without any enzyme involved in the reaction.

In this invention, organic solvents were used in enzymatic hydrolysis of lecithins for better controlling the conversion of PI to LPI. LPI conversion was able to reach >90% when certain organic solvents were used together with small quantity of water. Over hydrolysis of PI to GPI was not observed. A straightforward work up procedure was also invented in this invention to enrich LPI at high yield.

1. Cabezas, Dario & Diehl, Bernd & Tomás, Mabel. (2015). Emulsifying properties of hydrolysed and low HLB sunflower lecithin mixtures. European Journal of Lipid Science and Technology. 118. 10.1002.
2. JP2010063470A, 2019. Method for production of high-purity lysophosphatidylinositol and glycolipid.
3. US Patent 20050227945A1, 2005. Enzymatic modification of lecithin.
4. Aiba, Toshihiko et al. (2016). Regioselective Phosphorylation of myo-Inositol with BINOL-Derived Phosphoramidites, and its Application for Protozoan Lysophosphatidylinositol. Org. Biomol. Chem. 14. 10.1039.
5. Patent WO 2019/040992 A1, 2019. Synthetic derivatives of oleoyl-lysophosphatidyl inositol (oleolyl-lpi) and uses thereof.

The following examples are offered to illustrate but not limit the invention. Thus, it is presented with the understanding that various formulation modifications as well as method of delivery modifications may be made and still are within the spirit of the invention.

Example 1

Materials and Methods
Chemicals and Reagents.

Soy lecithin with PC content around 15% (PC15) and 30% (PC30 were bought from Meryas Lecithin Co. Ltd, Beijing, China. PC30 was in power form. Phospholipase $A_1$—Lecitase Ultra was also obtained from Kemin China. It was produced by Novozyme and currently used for the on-site production of Lysoforte concentrate liquid (LCL) in Kemin industrial China. Thin layer chromatography plate (silica gel matrix, aluminum foil backing, 20×20 cm), flash-chromatography column (50 mm×60 cm, with fritted disc) and silica gel (100-200 mesh) were purchased from Sigma-Aldrich. All organic solvents were of HPLC grade if not mentioned specifically.

Phospholipase $A_1$-Catalyzed Hydrolysis of Lecithin in Organic Solvents

This assay was developed to screen reaction parameters for the hydrolysis of lecithin. To a 20 mL sealed test tube 0.2 g lecithin and 2 mL organic solvent was added. The mixture was heated on 30-40° C. water bath and agitated occasionally in order to dissolve lecithin as much as possible. It was then heated on a 50° C. water bath. Leictase Ultra was diluted to 50% with ultrapure deionized water and added to the mixture according to the dosage level.

The mixture was continuously incubated at 50° C. and sampled after 1 hr, 2 hrs and 4 hrs for thin layer chromatography (TLC) analysis (described later). The TLC could semi-quantitatively determine the conversion of lecithin to lysolecithin. In order to get maximum conversion with least dosage of Lecitase Ultra, the assay was repeated several times by varying the solvent, concentration of substrate and enzyme dosage.

Thin Layer Chromatography.

lecithin and lysolecithin standards, reaction mixtures and fractions from flash chromatography were diluted to about 10 mg/mL with dichloromethane (DCM). They were then spotted to a 6×3 cm TLC plate and dried by hair dryer. The TLC plate was placed in a glass chamber for development. A mixture of DCM:methanol:water (75:25:4, v/v/v) was used as developing solvent. When the developing solvent approached the top edge of TLC plate, it was taken out, dried and stained with 2.5% phosphomolybdic acid in ethanol. The stained TLC plate was finally heated on hot plate or by hair dryer to allow color development, PC and LPC were displayed as green spot on the TLC plate.

Enzymatic hydrolysis of lecithins. The hydrolysis of lecithins consists of three major steps—reaction, work-up and quick purification. 1) Reaction: PC15 or PC30 (10 g each) was weighed to a 150 mL conical flask with ground glass joint respectively. To each flask was added 50 mL ethyl acetate (EtOAc). The flask was plugged with ground glass stopper. The mixture was then heated to 50° C. and stirred by magnetic stirring bar until lecithin was all dissolved, followed by the addition of 2.5 mL 10% Lecitase Ultra in water. After 2 hr incubation, the mixture was cooled to room temperature by water bath immediately. Most LPC would precipitate out and form a sticky solid layer on the bottom of the flask. 2) Work-up: After 10 min settling to allow separation between organic phase and solid layer, the top organic phase was decanted. The precipitate was washed again by another portion of EtOAc (50 mL). Ethanol (50 mL) was then added to solubilize LPC at 50° C. The hot solution or slurry was filtered. The filtrate was collected and evaporated to dryness to afford product.

$^{31}$P-NMR and HPLC Analysis.

$^{31}$P-NMR was run by Spectral Service AG in Germany. It gave the molar ratio of phospholipid and lysophospholipid molecules to an internal standard, triphenyl phosphate $(PPh_3)$[10]. The weight percent of each molecule could be calculated based on their molecular weight and molar ratio from $^{31}$P-NMR. An HPLC-ELSD method was used for the quantification of LPI, LPC, PI, and PC as described by previous study[13]

Results

Solvents Screening for the Enzymatic Hydrolysis of Lecithin.

Nine organic solvents were tested for the enzymatic hydrolysis (Table 2). As a reactant, a very small amount of water was added to avoid O/W emulsion. PC shows good solubility in methanol (MeOH), ethanol (EtOH), methyl tert-butyl ether (MTBE), dichloromethane (DCM), ethyl acetate (EtOAc) and hexanes when heated up to 50° C. It is a little soluble in isopropyl alcohol (iPrOH) and barely soluble in acetone. The conversion was estimated by ratio of lecithin/(lecithin+lysolecithin) on the thin layer chromatography (TLC) plate. MTBE and EtOAc are found to be very good solvent for the enzymatic hydrolysis of lecithins. They both gave >90% conversion. More interestingly, there are precipitates in both solvents and we find most LPI product stays in the precipitate whereas fatty acids stay in the solvent, allowing the enrichment of LPI by simply decanting the organic layer.

TABLE 2

Solubility and conversion of lecithin in organic solvent.

| Solvent | MeOH | EtOH | iPrOH | MTBE | DCM | Acetone | EtOAc | Hexanes |
|---|---|---|---|---|---|---|---|---|
| Solubility of lecithin at 50° C. | good | good | low | Good | good | very low | good | Good |
| Conversion of lecithin to lysolecithin | 30% | 30% | 20% | 90% | 20% | 5% | 90% | 20% |

Enzymatic Synthesis of LPI-Enriched Lysolecithin.

Two soy lecithin samples of different grade, PC15 and PC30 (10 g each) were used as starting material for the synthesis of LPI-enriched lysolecithin. Crude products from them were labeled as LPC15 and LPC30 respectively.

The synthetic results are listed in Table 3. PI was not even detectable in all samples. LPI reached 6% and 9.6% respectively. Both LPC and LPE were also found enriched to >10% while LPA was enriched to >2.9%.

TABLE 3

Phospholipid profile of high-LPI lysolecithin products from enzymatic hydrolysis (%).

| Product # | From PC15 | From PC30 |
|---|---|---|
| PC | 1.4 | 1 |
| PE | 0.8 | 1.3 |
| PA | 0.3 | 0.3 |
| 1-LPC | 6.6 | 4.6 |
| 2-LPC | 17.5 | 11.7 |
| LPI | 6 | 9.6 |
| LPE | 11.1 | 14.6 |
| LPA | 2.9 | 4.4 |
| Other phospholipids | 12.6 | 8.1 |
| Total phospholipids | 59 | 55.7 |

Discussion

This paper demonstrates a facile way to obtain high-LPI lysolecithin in gram scale by enzymatic synthesis.

Comparing to the enzymatic synthesis of LCL, the major changes in this new enzymatic synthesis are: it uses ethyl acetate as solvent, it fully converted PI to LPI and it enriches LPC/LPE/LPA during the process. Lecitase Ultra, a phospholipase $A_1$ used in LCL, functions very well in organic solvents like methylter-butyl ether and ethyl acetate.

This new enzymatic synthesis consists of all easy-handling steps: reaction, decanting, washing and filtration. No complicated purification process is needed. The reaction step requires a small amount of water for the hydrolysis process, so the moisture in open air would not be a problem for the synthesis. Moreover, no mixed solvent is used all through the process. Ethyl acetate could be easily distilled separately and reused for next batches of synthesis. It possesses the property of a scalable reaction. It can be scaled up to kilo or hundred kilos scale after necessary modifications.

REFERENCES

1. Tsuzuki W., Ue A., Nagao A., Endo M. and Abe M. 2004. Inhibitory effect of lysophosphatidylcholine on pancreatic lipase-mediated hydrolysis in lipid emulsion. Biochim Biophys Acta; 1684(1-3): 1-7. SA-13-00254.
2. Lakshminarayana R., Raju M., Krishnakantha T. P. and Baskaran V. 2006, Enhanced lutein bioavailability by lyso-phosphatidylcholine in rats. Molecular and Cellular Biochemistry; 281(1&2): 103-110. SA-08-05860.
3. Yahagi S., Koike M., Okano Y. and Masaki H. 2011. Lysophospholipids improve skin moisturization by modulating of calcium-dependent cell differentiation pathway. Int J Cosmet Sci; 33(3): 251-6. SA-11-01284.
4. Nakano T., Inoue I., Katayama S., Seo M., Takahashi S., Hokari S., Shinozaki R., Hatayama K. and Komoda T. 2009. Lysophosphatidylcholine for efficient intestinal lipid absorption and lipoprotein secretion in Caco-2 cells. Journal of Clinical Biochemistry and Nutrition; 45(2): 227-234. SA-13-00255.
5. D'Arrigo P. and Servi S. 2010. Synthesis of lysophospholipids. Molecules; 15(3): 1354-77. SA-12-01498.
6. Virto C. and Adlercreutz P. 2000. Lysophosphatidylcholine synthesis with *Candida antarctica* lipase B (Novozym 435). Enzyme and Microbial Technology; 26(8): 630-635. SA-09-04161.
7. Yao L. and Jung S. 2010. $^{31}$P NMR phospholipid profiling of soybean emulsion recovered from aqueous extraction. J Agric Food Chem; 58(8): 4866-72. SA-11-01124.

Example 2

Chemicals and Reagents.

De-oiled powdery lecithin (light yellow powder) containing high phosphatidylinositol (PI, 24%) and less phosphatidylcholine (PC, 5%) was purchased from Maxim Biotechnology Co., Ltd, Jiangsu, China; phospholipase $A_1$ (Lecitase Ultra, Novozymes, Lot #1801106600) and ethyl acetate (AR grade, 99%) and regular soy lecithin were used from Kemin China; $NaH_2PO_4 \cdot 2H_2O$ and $Na_2HPO_4 \cdot 12H_2O$ (AR grade) were purchased from Guangzhou Chemical Reagents Factory. All organic solvents were of HPLC grade if not mentioned specifically.

Equipment.

Magnetic stirrer with water heater (Shanghai Lichenbangxi Instruments Co., Ltd); electronic balance; electric stirrer (IKA RW20, German); oven, vacuum oven, water bath (Shanghai Yiheng Instruments Co., Ltd)

Preparation of Phosphate Buffer (PBS, pH 7.0, 0.1 M).

20.66 g of $Na_2HPO_4 \cdot 12H_2O$ and 6.6 g of $NaH_2PO_4 \cdot 2H_2O$ were dissolved in 950 ml deionized water, and adjusted pH 7.0, followed by dilution to 1000 ml.

Synthesis of High-LPI Lysolecithin at Lab Scale.

The general synthetic procedure at lab scale was conducted according to the method described by Huang with some modifications[12]. Briefly, 12.5 g of de-oiled lecithin or regular soy lecithin were weighed and placed into a 250 mL round bottom flask. Ethyl acetate (EtOAc), PBS and phospholipase $A_1$ ($PLA_1$) were added into the flask. The mixture was then heated to 50° C. and stirred by an electronic mixer for different times (0.5, 1, 2, 3, 4 h). After the reaction $PLA_1$ was de-activated at 70° C. for 30 minutes. Then the mixture was immediately cooled to about 40° C. by a water bath and left to settle for 60 min to allow phase separation. Lysolecithin settled into the aqueous phase to form a sticky layer on the bottom of the flask, while the oil and free fatty acid stayed in the EtOAc organic phase on top. The aqueous phase was collected and dried in a vacuum oven at 65° C. for 12 hours to afford a crude lysolecithin powder containing higher LPI (noted as high-LPI lysolecithin). The organic phase was discarded.

Effects of Reaction Conditions on the Conversion of LPI.

Four factors on the hydrolysis degree were evaluated as below: reaction time (0.5, 1.0, 1.5, 2, 3, and 4 h), reaction temperature (40° C., 50° C., 60° C., and 65° C.), EtOAc volume (300%, 500%, 750% and 1000% of lecithin, volume to lecithin weight, v/w), and PBS content (20%, 40%, 60% and 100%, weight to lecithin weight, w/w). Samples were withdrawn from the reaction mixture and dried in a vacuum oven for the quantification of LPI and LPC contents.

Optimization of the Reaction Parameters by Applying Orthogonal Experimental Design.

Reaction time, PBS content, EtOAc volume and $PLA_1$ dosage were chosen for further optimization. Temperature was not chosen as one of the optimization factors because $PLA_1$ was determined to have optimal catalytic activity at 50° C. To explore the optimal combination of these four factors, an orthogonal design $L_9$ ($3^4$) was applied. The experimental details for using de-oiled lecithin as the starting material is given in Table 4 & 5. The detailed information for using regular soy lecithin as the starting material is listed in Table 6 & 7. Samples were withdrawn from the reaction mixture and dried at vacuum oven for the quantification of LPI and LPC levels.

TABLE 4

Factors and levels of orthogonal experimental design for converting de-oiled lecithin to high-LPI lysolecithin

| Factors | Levels | | |
| --- | --- | --- | --- |
| | 1 | 2 | 3 |
| PBS (%, w/w) | 20 | 60 | 120 |
| $PLA_1$ (%, w/w) | 0.2 | 0.4 | 0.8 |
| EtOAc (%, v/w) | 500 | 800 | 1200 |
| Reaction time (h) | 1 | 2 | 4 |

Note:
The content of PBS, $PLA_1$ and EtOAc was calculated based on lecithin weight

TABLE 5

The experimental details of orthogonal experimental design for converting de-oiled lecithin to high-LPI lysolecithin

| Entry | PBS (%) | $PLA_1$ (%) | EtOAc (%) | Reaction time (h) |
| --- | --- | --- | --- | --- |
| 1 | 20 | 0.2 | 500 | 1 |
| 2 | 20 | 0.4 | 800 | 2 |
| 3 | 20 | 0.8 | 1200 | 4 |
| 4 | 60 | 0.2 | 800 | 4 |
| 5 | 60 | 0.4 | 1200 | 1 |
| 6 | 60 | 0.8 | 500 | 2 |
| 7 | 120 | 0.2 | 1200 | 2 |
| 8 | 120 | 0.4 | 500 | 4 |
| 9 | 120 | 0.8 | 800 | 1 |

TABLE 6

Factors and levels of orthogonal experimental design for converting regular soy lecithin to high-LPI lysolecithin

| Factors | Levels | | |
| --- | --- | --- | --- |
| | 1 | 2 | 3 |
| PBS (%) | 20 | 60 | 100 |
| $PLA_1$ (%) | 0.2 | 0.4 | 0.8 |
| EtOAc (%) | 500 | 800 | 1200 |
| Reaction time (h) | 1 | 2 | 4 |

Note:
The content of PBS, $PLA_1$ and EtOAc was calculated based on lecithin weight

TABLE 7

The experimental details of orthogonal experimental design for converting regular soy lecithin to high-LPI lysolecithin

| Entry | PBS (%) | $PLA_1$ (%) | EtOAc (%) | Reaction time (h) |
| --- | --- | --- | --- | --- |
| 1 | 20 | 0.2 | 500 | 1 |
| 2 | 20 | 0.4 | 800 | 2 |
| 3 | 20 | 0.8 | 1200 | 4 |
| 4 | 60 | 0.2 | 800 | 4 |
| 5 | 60 | 0.4 | 1200 | 1 |
| 6 | 60 | 0.8 | 500 | 2 |
| 7 | 100 | 0.2 | 1200 | 2 |
| 8 | 100 | 0.4 | 500 | 4 |
| 9 | 100 | 0.8 | 800 | 1 |

Repeat Small-Scale Synthesis Under Optimized Conditions.

250 g of de-oiled lecithin or regular soy lecithin were added into a round bottom flask (2.5 L), followed by the addition of optimal PBS, PLAT, and EtOAc. The mixture was vigorously mixed with a top-driven screw impeller at 600 revolutions per minute (rpm). Sample preparation and analysis were performed using the same way as mentioned in the above sections.

Pilot Production of High-LPI Lysolecithin.

Three batches of production were performed in Hongji Photoelectric Material Co., Ltd. Fuxin, Liaoning Province, China. Regular soy lecithin was used as the starting material. The optimal conditions were applied for pilot production. Briefly, 250 kg regular soy lecithin, 75 kg PBS, 800 kg EtOAc and 0.5 kg $PLA_1$ were loaded into an enamel reactor (2000 L). The reactor was equipped with a spiral mixer, a temperature controller, and a vacuum distillation system. The flow chart for pilot production of high-LPI lysolecithin is shown in FIG. 1. After reaction at 50° C. for 4 hours, $PLA_1$ was de-activated at 75° C. for 30 min in the reactor. The aqueous phase containing lysolecithin, PBS and minor EtOAc was discharged from the bottom of the reactor. It was condensed and then put on stainless-steel trays and dried in a steam oven. Samples were withdrawn from reaction mixture at 2 h, 3 h and 4 h and dried in oven for the quantification of LPI and LPC level. The product after oven drying was also collected for LPI and LPC analysis.

High-Performance Liquid Chromatography (HPLC) Analysis of Phospholipids.

An HPLC-ELSD method was used for the quantification of LPI, LPC, PI, and PC as described by previous study.

Results

Effects of Reaction Conditions on the Conversion of LPI.

Figure 2:
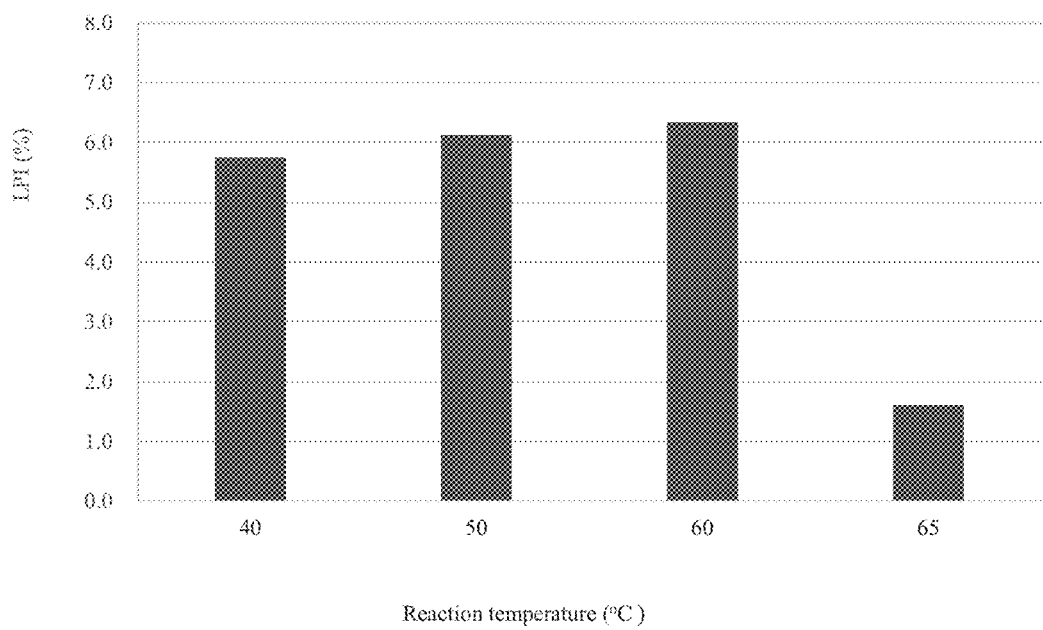
FIG. 2 is a graph illustrating the effects of reaction temperature on LPI content as described in Example 2.
Figure 3:
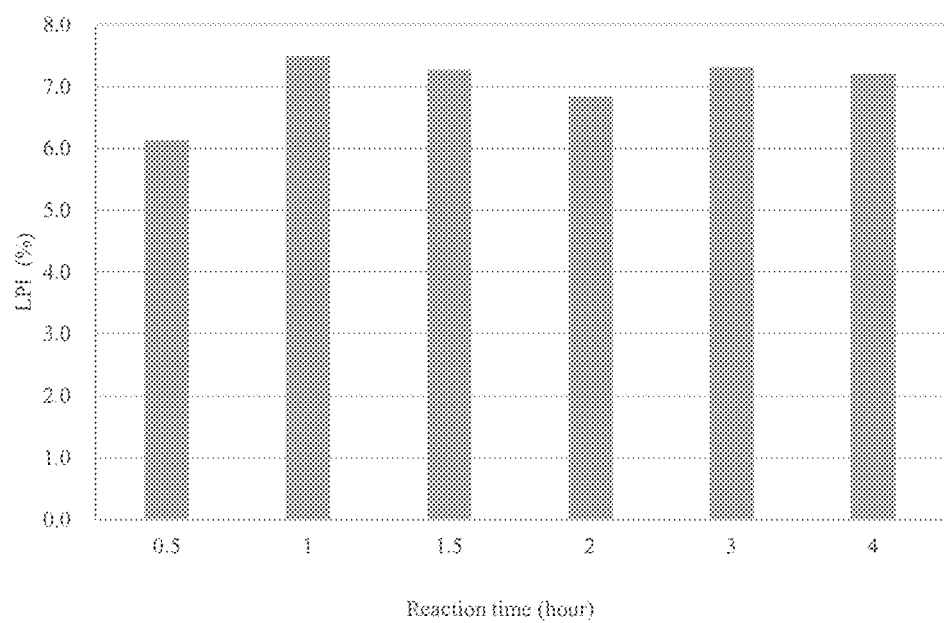
FIG. 3 is a graph illustrating the effects of reaction time on LPI content as described in Example 2.
Figure 4:
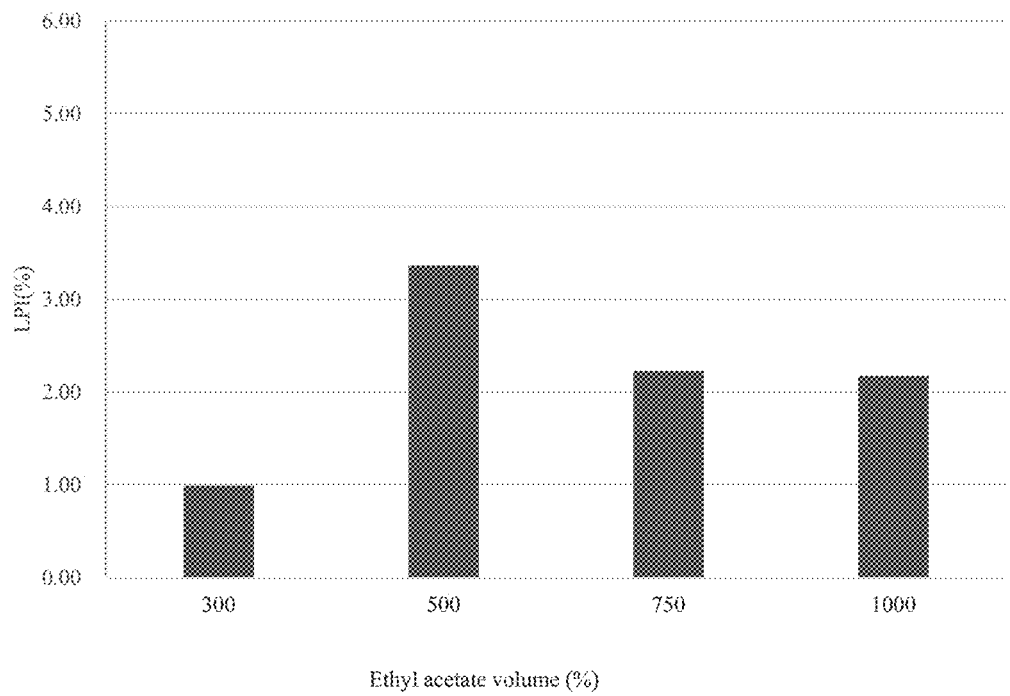
FIG. 4 is a graph illustrating the effects of ethyl acetate volume on LPI content as described in Example 2.
Figure 5:
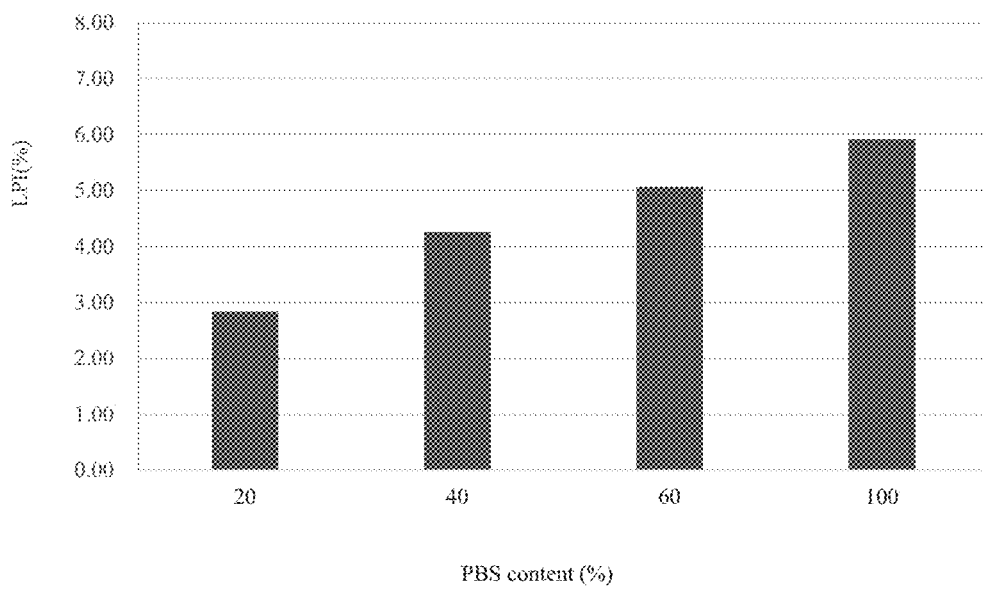
FIG. 5 is a graph illustrating the effects of PBS content on LPI content.

The results of reaction temperature are shown in FIG. 2. The LPI content increased slightly with the increase of temperature, but when the temperature increased to 65° C., the LPI content dropped sharply. It was probably due to the inactivation of $PLA_1$ at high temperature. In terms of reaction time, LPI content increased rapidly to 6.1% within 30 minutes and maintained at about 7.3% within the following 4 hours (FIG. 3). In this experiment, the highest LPI content was observed at a ratio of EtOAc to lecithin of 500% (v/w) (FIG. 4). There was a linear increase of LPI content along with PBS increase (FIG. 5).

Figure 6:
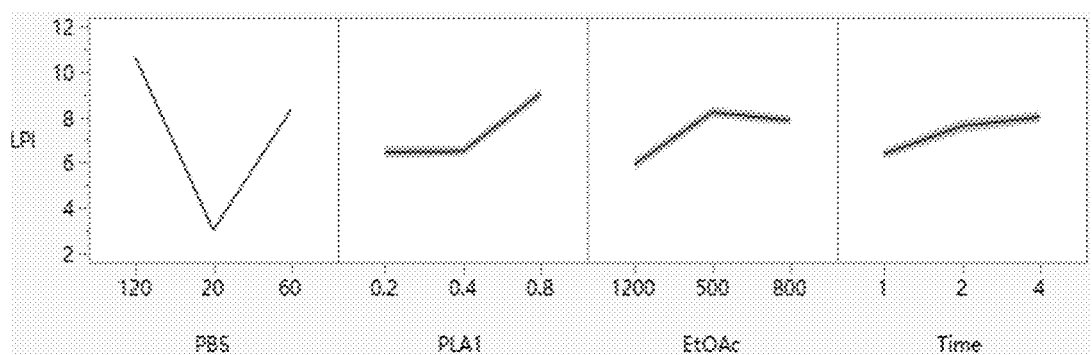
FIG. 6 is a graph illustrating the influence of the four factors of PBS, PLA1, EtOAc, and Time on LPI content using de-oiled lecithin as the starting material, as set forth in Example 2.
Figure 7:
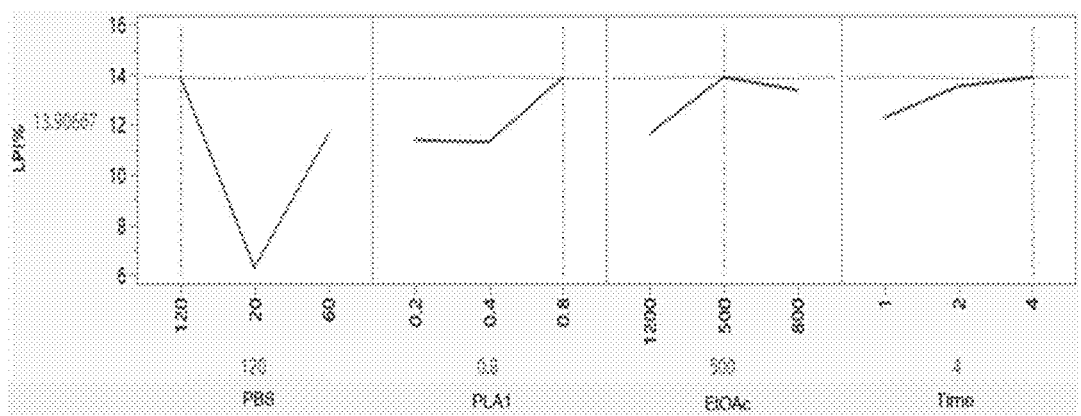
FIG. 7 is the predicted highest LPI content (13.9%) under the suggested conditions as set forth in Example 2.

Optimization of Reaction Conditions for Converting De-Oiled Lecithin to High-LPI Lysolecithin. When using de-oiled lecithin as the starting material; LPI and PI levels under different reaction conditions are shown in Table 8. LPI contents obtained in Entries 6, 8, 9 are above 11%, which are much higher than that obtained in other entries. The influence of the factors on LPI level ranked as $PBS>PLA_1>EtOAc>Reaction$ time (FIG. 6). Yields for most entries were close to 80%. The predicted highest LPI content was obtained under the conditions displayed in FIG. 7. To balance the LPI content and production costs, the optimal condition was established as below: 80% PBS, 0.4% $PLA_1$, 500% EtOAc and reaction for 4 hours. Repeated synthesis under these optimal conditions afforded 10.0-13.1% LPI content lysolecithin as displayed in FIG. 8.

TABLE 8

Effects of different reaction conditions on converting de-oiled lecithin to high-LPI lysolecithin

| Entry | PBS (%) | $PLA_1$ (%) | EtOAc (%) | Reaction time (h) | LPI (%) | PI (%) | LPC (%) | Yield (%) |
|---|---|---|---|---|---|---|---|---|
| 1 | 20 | 0.2 | 500 | 1 | 2.18 | 17.38 | 2.24 | 83.56 |
| 2 | 20 | 0.4 | 800 | 2 | 2.84 | 18.32 | 2.69 | 81.16 |
| 3 | 20 | 0.8 | 1200 | 4 | 4.05 | 15.42 | 3.25 | 64.36 |
| 4 | 60 | 0.2 | 800 | 4 | 8.62 | 9.77 | 3.65 | 74.60 |
| 5 | 60 | 0.4 | 1200 | 1 | 5.18 | 15.18 | 3.28 | 78.04 |
| 6 | 60 | 0.8 | 500 | 2 | 11.28 | 3.24 | 4.44 | 79.12 |
| 7 | 120 | 0.2 | 1200 | 2 | 8.78 | 9.91 | 3.75 | 79.04 |
| 8 | 120 | 0.4 | 500 | 4 | 11.32 | 1.06 | 4.28 | 76.44 |
| 9 | 120 | 0.8 | 800 | 1 | 11.77 | 3.04 | 4.25 | 76.96 |

Figure 9:
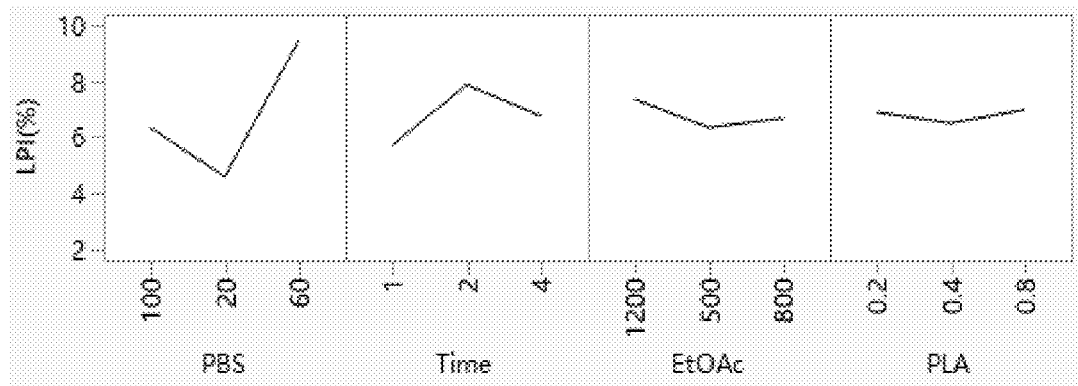
FIG. 9 is a graph illustrating the effects of PBS, Time, EtOAc and PLA on LPI content using regular soy lecithin as the starting material, as set forth in Example 2.

Optimization of reaction conditions for converting regular soy lecithin to high-LPI lysolecithin. The LPI contents under different reaction conditions of orthogonal experimental design are shown in Table 9. The LPI contents in Entries 4, 6 and 7 were much higher than that the other entries. The influence of the four factors on LPI contents ranked as: $PBS>Time>EtOAc>PLA_1$ (FIG. 9). To balance the LPI content and production cost, the optimal conditions were proposed as: PBS (60%), reaction time (4 h), EtOAc (500%), and $PLA_1$ (0.2%). Besides high LPI content, LPC contents in the high-LPI lysolecithin also reached to 15-16% in the Entry 4-6. Yields for all entries were about 50%. Repeated synthesis under these optimal conditions afforded 6.5-7.7% LPI and 13.6-15.8% LPC content lysolecithin as displayed in FIG. 10.

TABLE 9

Effects of different reaction conditions on converting regular soy lecithin to high LPI lysolecithin

| Entry | PBS (%) | $PLA_1$ (%) | EtOAc (%) | Time (h) | LPI (%) | LPC (%) | Yield (%) |
|---|---|---|---|---|---|---|---|
| 1 | 20 | 0.2 | 500 | 1 | 3.23 | 8.91 | 50.0 |
| 2 | 20 | 0.4 | 800 | 2 | 5.27 | 9.74 | 50.0 |
| 3 | 20 | 0.8 | 1200 | 4 | 5.26 | 9.43 | 50.0 |
| 4 | 60 | 0.2 | 800 | 4 | 9.31 | 16.35 | 44.3 |
| 5 | 60 | 0.4 | 1200 | 1 | 8.7 | 15.7 | 43.7 |
| 6 | 60 | 0.8 | 500 | 2 | 10.31 | 15.23 | 46.2 |
| 7 | 100 | 0.2 | 1200 | 2 | 8.04 | 15.05 | 45.2 |
| 8 | 100 | 0.4 | 500 | 4 | 5.67 | 7.48 | 50.0 |
| 9 | 100 | 0.8 | 800 | 1 | 5.37 | 9.23 | 50.0 |

Pilot production of high-LPI lysolecithin. LPI contents in the high-LPI lysolecithin product from three batches of pilot production are given in Table 10. LPI contents increased rapidly within the first 2 hours of enzymatic reaction, and the final LPI contents in the three batches of production ranged from 5.8% to 6.8%, which was close to that obtained at lab-scale experiments. Production yields ranged from 56% to 71%. It was also observed that higher LPC contents in the high-LPI lysolecithin, which were ranged from 10% to 15% (Table 11). Batch 2 and 3 had lower contents of LPI and LPC but the yields were higher. The overall mass weight of LPI from all three batches were quite close. The recovery of ethyl acetate was about 87% which could be further optimized to bring down solvent cost. The waste from the organic phase (oil, free fatty acid, and minor ethyl acetate) needs further investigation to determine if it is environmentally friendly.

TABLE 10

LP1 content in the high-LPI lysolecithin product from three batches of pilot production

| Batch No. | LPI content (%) | | | Yield (%) |
|---|---|---|---|---|
| | 2 h | 3 h | 4 h | |
| 1* | 6.29 | / | 6.83 | 56.72 |
| 2* | 5.50 | 6.25 | 6.45 | 61.76 |
| 3* | 5.94 | 5.65 | 5.75 | 71.52 |

TABLE 11

LPC content in the high-LPI lysolecithin powder in three batches of pilot production

| Batch No. | LPC content (%) | | |
|---|---|---|---|
| | 2 h | 3 h | 4 h |
| 1* | 13.44 | / | 15.75 |
| 2* | 12.98 | 13.95 | 13.87 |
| 3* | 10.05 | 11.28 | 10.13 |

Discussion

Figure 8:
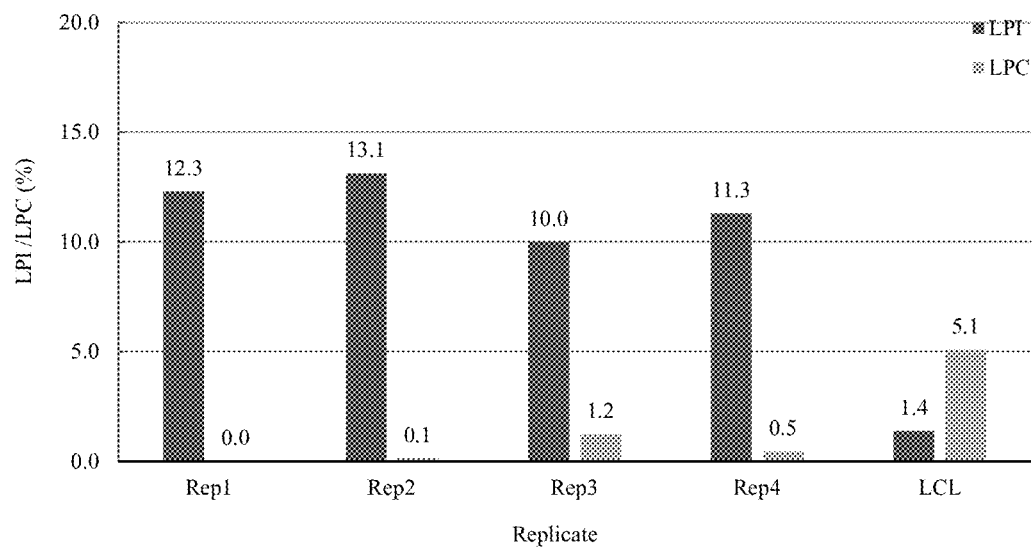
FIG. 8 is a graph illustrating LPI and LPC content in the repeating experiments under the optimal conditions when de-oiled lecithin is used as the starting material, as set forth in Example 2.

Although the LPI molecule has been widely used in research studies, the high-purity form was mostly obtained from a reagent company or chemical synthesis. Both required time-consuming purification steps like preparative HPLC. However, enzymatical hydrolysis is another way to obtain LPI from PI-containing lecithins. Literature has reported a variety of conditions for the hydrolysis of lecithin to form lysolecithins, whose composition was mainly claimed for the content of LPC. This study demonstrated the possibility of obtaining high LPI content lysolecithins through an organic phase enzymatic hydrolysis of de-oiled lecithin and regular soy lecithin. The reaction system was able to fully hydrolyze PI as well as enrich the hydrolyzed product (LPI) in the final product. Regardless of the starting materials, LPI contents in the lysolecithin prepared by this new method were at the range of 5.8-13.1%, which were 5-10 times higher than that in commercial lysolecithins. (FIG. 8). The method was also verified at 250 kg scale to produce bulk quantities of high-LPI lysolecithin.

This new enzymatic modification of lecithin consists of all easy-handling steps: reaction, phase separation, and drying. No complicated purification process is needed. Although many organic solvents were reported to tolerate enzymatic hydrolysis of lecithins[5-7,12], EtOAc was used in the process because it was environmentally friendly and quite acceptable in both food and feed industries. First, for the reaction itself, it required a small amount of water for the hydrolysis process, so the moisture in open air would not be a problem for the reaction. No mixed solvent was used all through the process. Ethyl acetate could be easily distilled separately and reused for subsequent batches. Second, the process did not contain any difficult or expensive purification steps. Lysolecithin automatically formed an emulsion in the aqueous phase and then was separated from the starting materials and free fatty acid by-product. Third, all raw materials used in the reaction were not expensive except phosphatase $A_1$. However, the dosage of $PLA_1$ was only 0.2% (w/w) so the overall cost was still very low.

Figure 10:
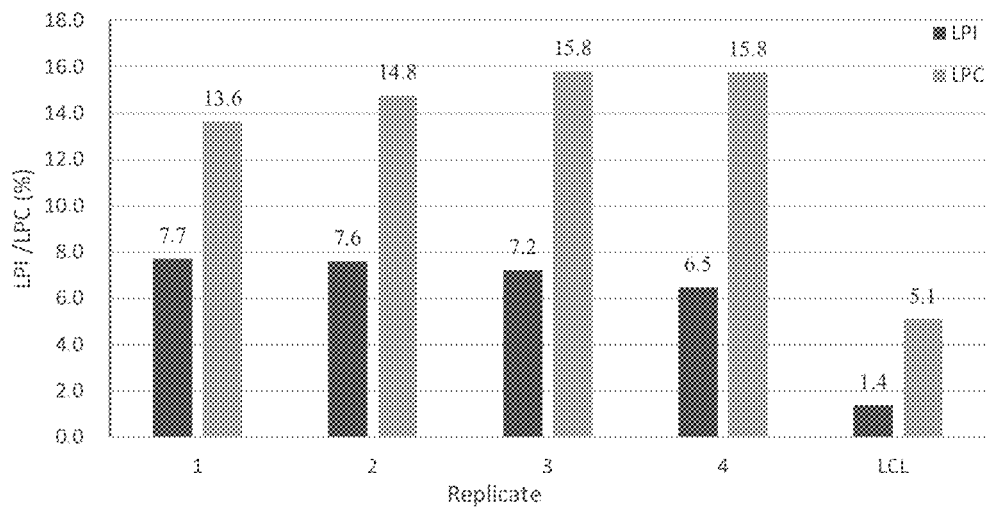
FIG. 10 is a graph illustrating the LPI and LPC content in the repeating experiments under the optimal reaction conditions when using regular soy lecithin as the starting material as set forth in Example 2.

In conclusion, this newly optimized enzymatic synthesis provided us a cost-effective, environmentally friendly and efficient way to prepare high-LPI lysolecithin. Products obtained from this synthesis without further purification contained as high as 13.1% LPI and 15.8% LPC. (FIGS. 8 and 10).

REFERENCES

1. Brautigan D L, Li R, Kubicka E, Turner S D, Garcia J S, Weintraut M L, and Wong E A. Lysolecithin as feed additive enhances collagen expression and villus length in the jejunum of broiler chickens. 2017, Poult. Sci. 96, 2889-2898.
2. U.S. Pat. No. 4,849,137, Kobayashi, Process for producing lysophospholipids containing substantially no lysophospholipids except LPC.
3. Hu Jie, Yu Bokai, Lu Fei et al. Preparation of Lysophospholipids by Phospholipase A1-Catalyzed Hydrolysis of Antarctic Krill Phospholipids in Aqueous Phase. Food Science, 2019, 40(12): 92-97.
4. Fan Kun, Yi Yanjie, Liu Yang et al. Preparation of soybean lysophospholipids and its biosafety analysis. CHINA OILS AND FATS. 2019, 44(6):124-127.
5. Juhan Kim, Chang-Soo Lee, Jongmin Oh, et al. Production of egg yolk lysolecithin with immobilized phospholipase A2. Enzyme and Microbial Technology, 2001.587-592.
6. Taha M, Hérault Josiane, Laurent G, et al. Lipase-catalyzed production of lysophospholipids. OCL, 2017, 24(4): D405.
7. U.S. Pat. No. 7,189,544, Schmitt et al., Enzymatic modification of lecithin.

Example 3

Materials and Methods
Chemicals and Reagents.

Phospholipase $A_1$ (Lecitase Ultra, Novozymes), regular soy lecithin and isopropyl acetate (Industry grade, 99%) were purchased from the local suppliers. Deionized water was prepared by the production factory.

Production of High-LPI Lysolecithin at Large Scale.

Six batches of production were conducted in a factory in Hunan province, China. Regular soy lecithin was used as the starting material. The optimal conditions were applied for scale-up production. Briefly, 450 kg regular soy lecithin, 135 kg deionized water, 1440 kg isopropyl acetate and 0.9 kg phospholipase $A_1$ were loaded into an stainless steel reactor (3000 L). The reactor was equipped with three sets of spiral spandles, a temperature controller, and a vacuum distillation system. The flow chart for scale-up production of high-LPI lysolecithin is shown below. After reaction at 50° C. for 2 hours, phospholipase $A_1$ was de-activated at 75° C. for 30 min in the reactor. The aqueous phase containing lysolecithin, water and small quantity of isopropyl acetate was discharged from the bottom of the reactor. It was condensed and then loaded with silica followed by drying on stainless-steel trays in a steam oven. The finished powdery product containing silica and lysolecithin were sampled each batch for the analysis of LPI and LPC, which was qualified with the HPLC-ELSD method mentioned in example 2.

Results

Figure 11:
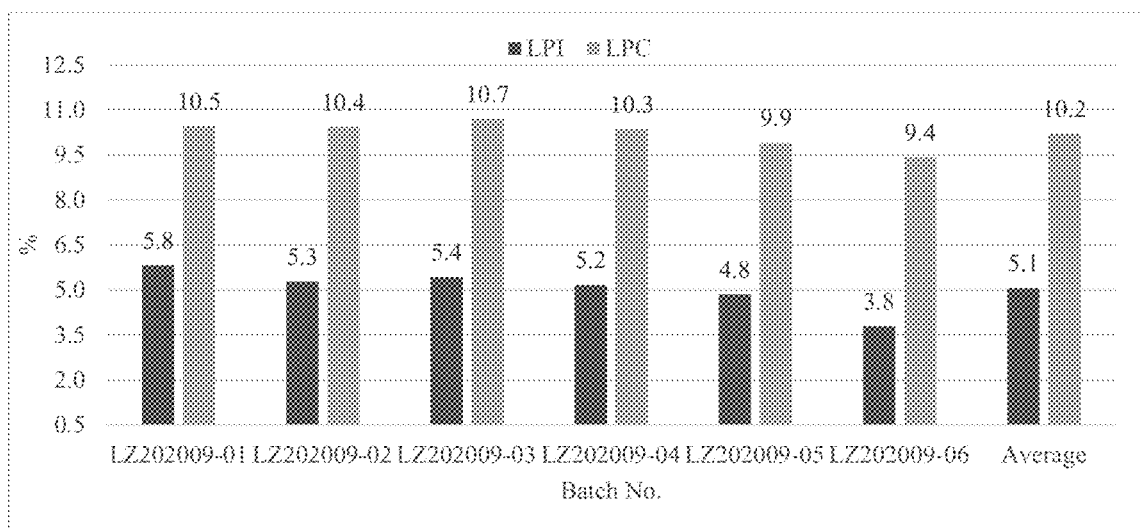
FIG. 11 is a graph illustrating the LPI and LPC content in the finished product as set forth in Example 3 which employed isopropyl acetate instead of acetyl acetate as the solvent.
Figure 12:
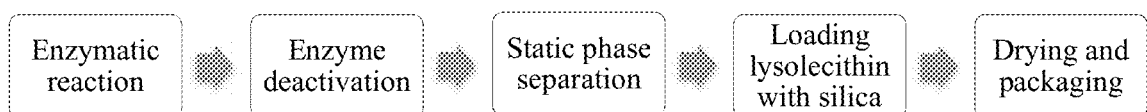
FIG. 12 is a flow chart illustrating the process of the present invention.

LPI and LPC content in the finished product (mixture of silica and lysolecithin) are shown in FIG. 11. LPI content in all batches of finished good were all higher than 3.5%. Except Batch LZ202009-06, LPI content were ranged from 4.8-5.8%. LPC content showed the same trends as LPI. For Batch LZ202009-06, LPI content was lower than that of other batches, the possible reason maybe attribute to the uncomplete enzymatic reaction indicated by more phosphatidylinositol (PI) residues than other batches. The results indicated that isopropyl acetate was a good solvent for the higher conversion of PC and PI to LPC to LPI. FIG. 12 depicts the process flow chart.

Mass balance for all 6 batches of pilot production are listed in Table 12. A total of 2356 kg high-LPI lysolecithin was obtained from 2770 kg of soy lecithin. Overall yield was 85%.

TABLE 12

The balance of materials for the pilot production of high-LPI lysolecithin powder (450 kg/batch)

| | Input | | | Output |
| --- | --- | --- | --- | --- |
| Batch No. | Lecithin (kg) | Isopropyl acetate (kg) [a] | Silica (kg) | Finished good (kg) |
| LZ202009-01 | 520 | 197 | 170 | 415 |
| LZ202009-02 | 450 | 197 | 153 | 379 |
| LZ202009-03 | 450 | 197 | 152 | 376 |
| LZ202009-04 | 450 | 197 | 153 | 395 |
| LZ202009-05 | 450 | 197 | 154 | 387 |
| LZ202009-06 | 450 | 197 | 158 | 405 |
| Total | 2770 | 1182 | 940 | 2356 |

[a] Average quantity per batch based on the total consumption.

Discussion

This newly developed enzymatic process for the preparation of high-LPI lysolecithin was proved feasible and robust at pilot scale using isopropyl acetate as the solvent. The average LPI and LPC content in the finished products reached 5.0% and 10.2% respectively. The yield reached 85%. Considering about 40% silica carrier was loaded in the finished product, the LPI an LPC content in the finished product can be much higher if we adjust the carrier ratio or even remove it.

It should be appreciated that minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

The foregoing description has been presented for the purposes of illustration and description. It is not intended to be an exhaustive list or limit the invention to the precise forms disclosed. It is contemplated that other alternative processes and methods obvious to those skilled in the art are considered included in the invention. The description is merely examples of embodiments. It is understood that any other modifications, substitutions, and/or additions may be made, which are within the intended spirit and scope of the disclosure. From the foregoing, it can be seen that the exemplary aspects of the disclosure accomplishes at least all of the intended objectives.

The invention claimed is:

1. A method of producing high-LPI lysolecithin wherein resulting lysolecithin comprises at least 2.5% by weight LPI, wherein the method comprises the steps of:
    mixing a source of lecithin with an organic solvent, at least one buffer or water, and a phospholipase to form a reaction mixture;
    heating the reaction mixture to 40 to 65° C. for about 0.5 to 5 hours;
    cooling the reaction mixture to 40° C. or below to separate the high-LPI lysolecithin from the reaction mixture; and
    collecting the high-LPI lysolecithin.

2. The method of claim 1 further comprising the step of drying the high-LPI lysolecithin to a moisture content of 10% or less.

3. The method of claim 1 wherein the organic solvent is an acetate or an ether.

4. The method of claim 1 wherein the organic solvent is selected from the group consisting of ethyl acetate (EtOAc), methyl tert-butyl ether and isopropyl acetate (iPrOAc).

5. The method of claim 1 wherein the phospholipase is phospholipase A1 (PLA1).

6. The method of claim 1 wherein the at least one buffer is a phosphate buffer.

7. The method of claim 6 wherein the phosphate buffer is phosphate buffered solution (PBS).

8. The method of claim 1 wherein the organic solvent is included in an amount of at least about 100% volume of organic solvent to lecithin weight.

9. The method of claim 7 wherein the organic solvent is included in an amount of between 300-600% volume of solvent to lecithin weight.

10. The method of claim 1 wherein the at least one buffer or water is included in an amount of at least about 1% by weight buffer or water to lecithin weight.

11. The method of claim 10 wherein the buffer or water is included in an amount of about 20-90% weight of buffer or water to lecithin weight being preferred.

12. The method of claim 5 wherein the PLA1 is included in an amount of at least about 0.1% by weight PLA1 to lecithin weight.

13. The method of claim 12 wherein the PLA1 is included in an amount of about 0.2-0.5% by weight PLA1 to lecithin weight being preferred.

14. The method of claim 1 wherein the mixture is heated to a temperature sufficient to cause hydrolysis of the lecithin to form a heated mixture.

15. The method of claim 14 wherein the mixture is heated to a temperature ranging from about 40-65° C. for a time period of about 0.5-5 hours.

16. The method of claim 14 further including the step of cooling the heated mixture for a period of time sufficient to allow lysolecithin to separate from the mixture.

17. The method of claim 16 further including the steps of collecting the lysolecithin and drying the lysolecithin.

18. The method of claim 17 wherein the lysolecithin is dried to a moisture content of about 10% by weight or less.

19. The method of claim 1 wherein the resulting lysolecithin comprise at least 0.0% and 2.0% by weight LPC and LPA, respectively.

20. The method of claim 3, wherein the organic solvent is ethyl acetate.

21. The method of claim 16, wherein the mixture is cooled to a temperature of 40° C. or less for a time period of at least 30 minutes.

22. The method of claim 1, wherein a lysophosphatidylinositol (LPI) content is increased from 1.4% to 6.5%.

* * * * *